United States Patent
Stockdale

(10) Patent No.: US 12,184,828 B2
(45) Date of Patent: Dec. 31, 2024

(54) APPARATUS, SYSTEM AND METHOD FOR FOAM DETECTION UTILIZING STEREO IMAGING

(71) Applicant: GLOBAL LIFE SCIENCES SOLUTIONS USA LLC, Marlborough, MA (US)

(72) Inventor: Alan Stockdale, Providence, RI (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 139 days.

(21) Appl. No.: 17/961,700

(22) Filed: Oct. 7, 2022

(65) Prior Publication Data

US 2024/0121372 A1 Apr. 11, 2024

(51) Int. Cl.
*H04N 13/271* (2018.01)
*H04N 13/204* (2018.01)
*H04N 13/00* (2018.01)

(52) U.S. Cl.
CPC ......... *H04N 13/271* (2018.05); *H04N 13/204* (2018.05); *H04N 2013/0081* (2013.01)

(58) Field of Classification Search
CPC ... C12M 41/02; H04N 13/271; H04N 13/204; H04N 2013/0081
See application file for complete search history.

(56) References Cited

U.S. PATENT DOCUMENTS

| | | | |
|---|---|---|---|
| 5,597,950 A | 1/1997 | Mullen | |
| 5,868,859 A | 2/1999 | Hei et al. | |
| 6,461,414 B1 | 10/2002 | Kohl et al. | |
| 9,550,971 B2 | 1/2017 | Niazi | |
| 9,809,793 B2 | 11/2017 | Riechers | |
| 9,908,664 B2 | 3/2018 | Galliher et al. | |
| 10,857,486 B2 | 12/2020 | Kisty | |
| 11,327,064 B2 | 5/2022 | Canty et al. | |
| 11,942,219 B1* | 3/2024 | McNair | G16H 50/30 |
| 2018/0252692 A1 | 9/2018 | Canty et al. | |
| 2020/0115669 A1 | 4/2020 | Bremer, Jr. | |
| 2021/0123010 A1* | 4/2021 | Gebauer | C12M 41/06 |

(Continued)

FOREIGN PATENT DOCUMENTS

| | | |
|---|---|---|
| CN | 103971379 A | 8/2014 |
| DE | 3727132 | 2/1989 |

(Continued)

OTHER PUBLICATIONS

Corresponding PCT Int. Search Report and Written Opinion dated Jan. 22, 2024.

(Continued)

*Primary Examiner* — Tsion B Owens
(74) *Attorney, Agent, or Firm* — Grogan, Tuccillo & Vanderleeden LLP

(57) ABSTRACT

A bioreactor system includes a housing configured to house and support a vessel, a stereo camera having first and second imagers secured to the housing, the stereo camera configured to image a surface of a liquid and a foam exposed to a headspace of the vessel. The system further includes a controller operatively connected to the stereo camera and the stereo camera and controller are configured to create an image of the exposed surface and identify foam on the surface based on the image.

24 Claims, 7 Drawing Sheets

(56) References Cited

U.S. PATENT DOCUMENTS

2022/0290090 A1\* 9/2022 Ball ................. C12M 41/26
2024/0027417 A1\* 1/2024 Vasefi ................. G01N 21/55

FOREIGN PATENT DOCUMENTS

| DE | 4036048 | 5/1991 |
| EP | 1950281 | 7/2008 |
| EP | 3044305 | 7/2016 |
| WO | 2021092049 A1 | 5/2021 |
| WO | 2022029163 A1 | 2/2022 |

OTHER PUBLICATIONS

Austerjost et al., "A Machine Vision Approach for Bioreactor Foam Sensing", Sls Technology, 2021, vol. 26(4) 408-414.
Hendriks, "The Improvement of Objective Milk Foam Quality Analysis Through Image Processing and Computer Vision", University of Twente Creative Technology, Jul. 8, 2020.
FoamDDI: Foam Digital Detection Imaging, Visaya, Jul. 29, 2020.

\* cited by examiner

APPARATUS, SYSTEM AND METHOD FOR FOAM DETECTION UTILIZING STEREO IMAGING

BACKGROUND

Technical Field

Embodiments of the invention relate generally to bioprocessing apparatus, systems, and methods, and more particularly, to observing and analyzing a fluid in a bioreactor utilizing stereo imaging to detect foam.

DISCUSSION OF ART

Bioreactors are often employed to carry out biochemical and/or biological processes and manipulate liquids and other products of such processes. Such bioreactors often include flexible or collapsible single-use disposable bags that are supported by an outer rigid structure such as a stainless-steel shell or frame. The bags are made of thin flexible sheets of plastic film and are positioned within the rigid shell and filled with the desired fluid for processing.

Growing biological materials such as mammalian cells, bacteria or yeast in bioreactor often results in the production of an unwanted foam layer which floats at the top of the fluid in the bioreactor, e.g., in a headspace of a bioreactor bag. This foam layer is the result of several factors including the addition of pressurized air to sustain aerobic microorganisms, nutrients and growth factors present in the liquid growth media, and waste products generated by the microorganisms. Over time, this foam layer may become unacceptably thick, and, if untreated, could potentially foul the exhaust port and filter of a bioreactor, prevent $CO_2$ from escaping, and negatively affect the structural integrity of the bag. Foam also forms a barrier to liquids injected from above the fluid in the bioreactor and is problematic even at low fluid volume levels.

To reduce the foam layer to a reasonable thickness, chemical solutions such as antifoam compounds are typically employed. With respect to such compounds, several applications may be needed during a single production run to ensure effectiveness. Conversely, too much antifoam compound can be detrimental to the biological materials in the reactor. Mechanical solutions, such as thermal probes and foam breakers also exist, however, they are more effective at reducing substantial amounts of existing foam rather than inhibiting foam formation.

In view of the above, accurate detection and monitoring of foam in a bioreactor bag is important to determine when intervention is necessary. While foam detection solutions exist, they only detect foam levels in a small area or, in some instances, at a single point in the bioreactor bag, rather than assessing the entirety of the exposed fluid surface in the bag. Moreover, many such systems have been found to be generally effective only for the detection of extreme foam events in which the biological materials, or the structure of bag itself, may already be compromised. Known solutions are also relatively large and expensive and do not function to ensure that, for example, the requisite amount of antifoam compound is applied in response to actual foam levels in a bag and do not have the capability to quantify the amount of foam present.

In view of the above, there is a need for an apparatus and system for observing a fluid in a bioreactor bag that provides for improved detection, monitoring, and mitigation of foam in the bag.

BRIEF DESCRIPTION

Certain embodiments commensurate in scope with the originally claimed subject matter are summarized below. These embodiments are not intended to limit the scope of the claimed subject matter, but rather these embodiments are intended only to provide a summary of the possible embodiments. Indeed, the disclosure may encompass a variety of forms that may be like or different from the embodiments set forth below.

In an embodiment, a foam identification system includes a stereo camera having first and second imagers configured to image a surface of a liquid and a foam in a vessel that is exposed to a headspace of the vessel. The system further includes a controller operatively connected to the stereo camera and the stereo camera and controller are configured to create an image of the exposed surface and identify foam on the surface based on the image.

In another embodiment, a bioreactor system includes a housing configured to house and support a vessel, a stereo camera having first and second imagers secured to the housing, the stereo camera configured to image a surface of a liquid and a foam exposed to a headspace of the vessel. The system further includes a controller operatively connected to the stereo camera and the stereo camera and controller are configured to create an image of the exposed surface and identify foam on the surface based on the image.

In yet another embodiment, a method of identifying foam on a surface of a liquid in a vessel includes the steps of generating an image of a surface of the liquid that is exposed to the headspace of the vessel via a stereo imaging camera having first and second imagers, and identifying foam on the exposed surface based on the image.

DRAWINGS

The present invention will be better understood from reading the following description of non-limiting embodiments, with reference to the attached drawings, wherein below:

DETAILED DESCRIPTION

Figure 1:
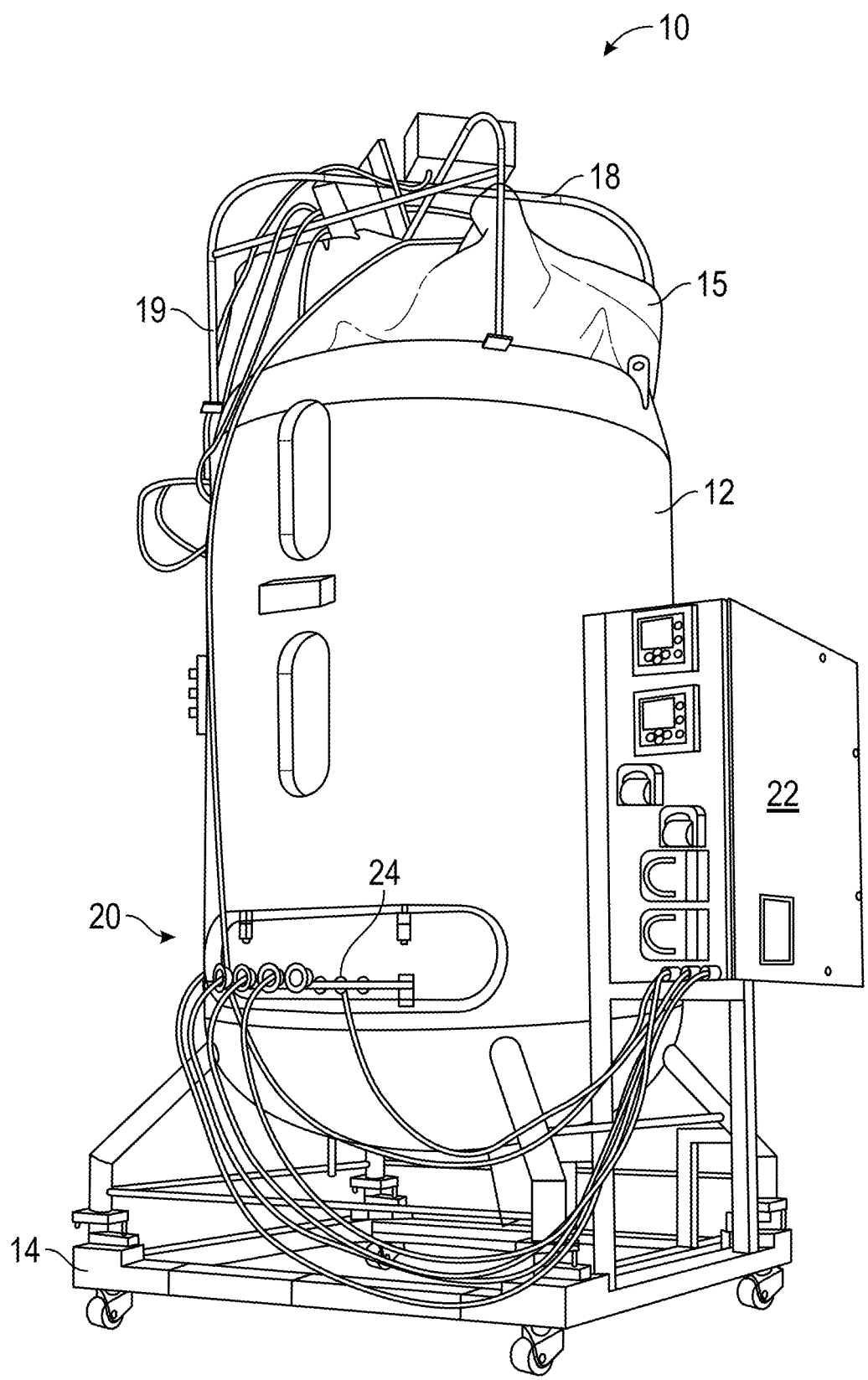
FIG. 1 is a front elevational view of a bioreactor system suitable for use with a foam identification system, according to an embodiment of the present invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, or a rigid container, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, fermentation systems, mixing systems, media/buffer preparation systems, and filtration/purification systems.

As used herein, the term "bag" means a flexible or semi-rigid container or vessel used, for example, as a bioreactor or mixer for the contents within. While embodiments of the present invention are described as for use with bioprocessing bags, including but not limited to bioreactor bags and mixer bags, embodiments may also be configured for use with other bags or vessels. Similarly, embodiments may be used to image, assess, and mitigate/treat other characteristics or conditions, in addition to the accumulation of foam in a bioreactor.

Further, while embodiments are described in connection with single use, stirred tank bioreactors and bioreactor systems, they are not limited to the same and may be used with a variety of vessels and associated equipment used in biological or biochemical processing. Additionally, embodiments may be suitable for use in identifying foam in other non-biological/biochemical contexts. Certain embodiments may be useful in detecting other non-foam related conditions or events on a surface that may be identified via stereo imaging as described herein.

With reference to FIG. 1, a bioreactor system 10 suitable for use with embodiments of the invention is illustrated. The bioreactor system 10 includes a generally rigid bioreactor housing 12 mounted atop a frame 14. The rigid housing 12 may be formed, for example, from stainless steel, polymers, composites, glass, or other metals, and may be cylindrical in shape, although other shapes may also be utilized without departing from the broader aspects of the invention. As will be appreciated, the housing is configured to house and support a vessel, e.g., bioreactor bag 15. In certain embodiments, the housing 12 may be a substantially rectangular mixer housing.

As shown, a single-use, flexible bioreactor bag 15 is disposed within the housing 12. As mentioned, the housing 12 can be any size (or shape) as long as it is capable of supporting a vessel such as a single-use flexible bioprocess bag 15. For example, according to one embodiment, the housing 12 is capable of accepting and supporting a 10-2000L flexible or collapsible bioprocess bag.

The bioreactor system 10 further includes a support structure 18 to which various equipment utilized in biochemical and/or biological processes are attached. The support structure 18 may also be used to lift and hold the bag 15 in place within the housing 12. The support structure 18 is shown as having a plurality of leg portions 19, but other configurations may be employed.

The housing 12 includes an opening or aperture 20 where, among other things, a temperature probe 24 can be inserted into a thermowell or port in the vessel 15 and then be coupled via e.g., a cable, to the instrument tower 22. As will be appreciated, the temperature probe 24 provides a temperature of a fluid in the vessel 15.

Figure 2:
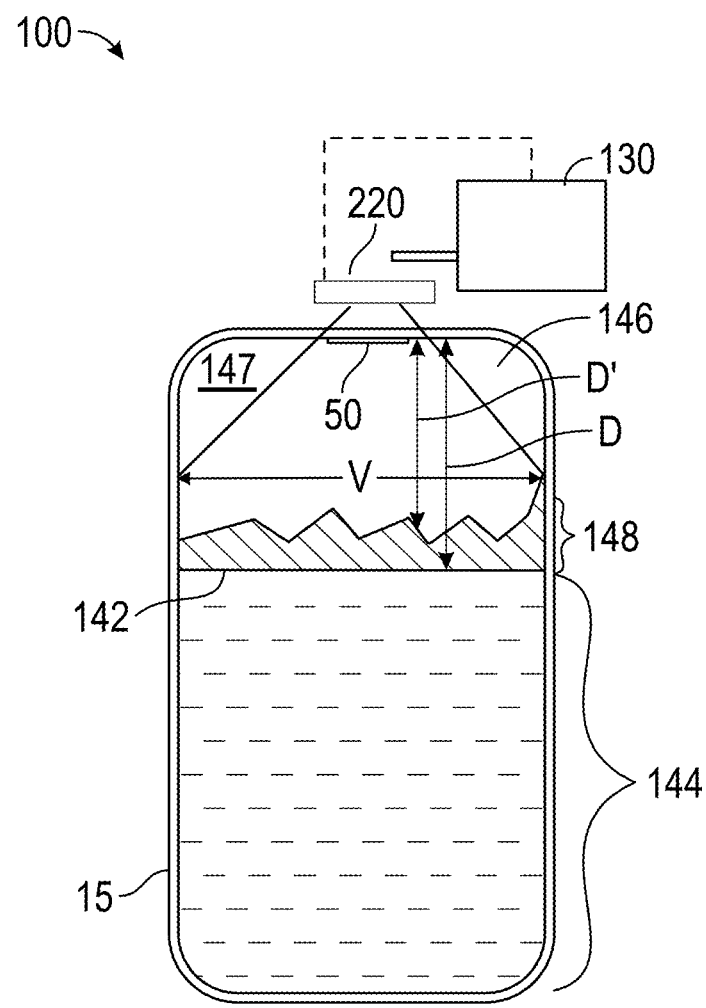
FIG. 2 is a diagram of a foam identification system, according to an embodiment of the present invention.

Referring now to FIG. 2, a foam identification system 100 according to an embodiment of the invention is depicted. As shown, the foam identification system 100 includes a stereo imaging camera 220 and a controller 130 operatively connected to the stereo imaging camera 220. In embodiments, the stereo imaging camera 220 is secured to the support structure 18 of the frame 14 (FIG. 1). As described in greater detail below, the stereo imaging camera 220 images a surface 142 of a liquid 144 in the vessel (e.g., bag) 15. In particular, the camera 220 images a surface 142 that is exposed to a headspace 146 of the vessel 15. The headspace 146 being the volume within the vessel 140 not occupied by liquid 144 or foam 148. The headspace 146 includes a gas 147, e.g., air, retained within the vessel 15, which is in contact with the exposed surface 142 of the liquid 144.

In embodiments, the stereo imaging camera 220 utilizes visible wavelength (380 nm to 700 nm) to image and calculate foam depth without requiring illumination. In certain embodiments that include an infrared projector, as discussed in greater detail below, the camera 220 may include sensors that measure up to infrared wavelengths of about 865 nm.

Significantly, the stereo imaging camera 220 sees a wide field of view V as opposed to a point source, which is important due to the unpredictable nature of foam buildup. In embodiments, the field of view V is substantially the entirety of the exposed surface 142. In certain embodiments, the stereo imaging camera 220 may utilize wide-angle lenses and may include auto-focus functionality. In embodiments, the camera 220 may image from about 70° to about 120° angle/field of view.

Figure 3:
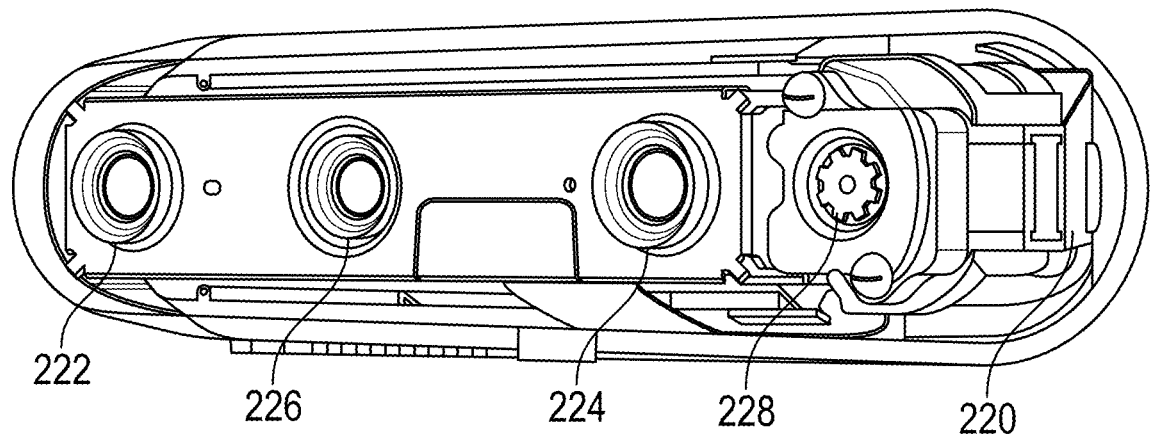
FIG. 3 is a perspective view of a stereo imaging camera, according to an embodiment of the present invention.
Figure 4:
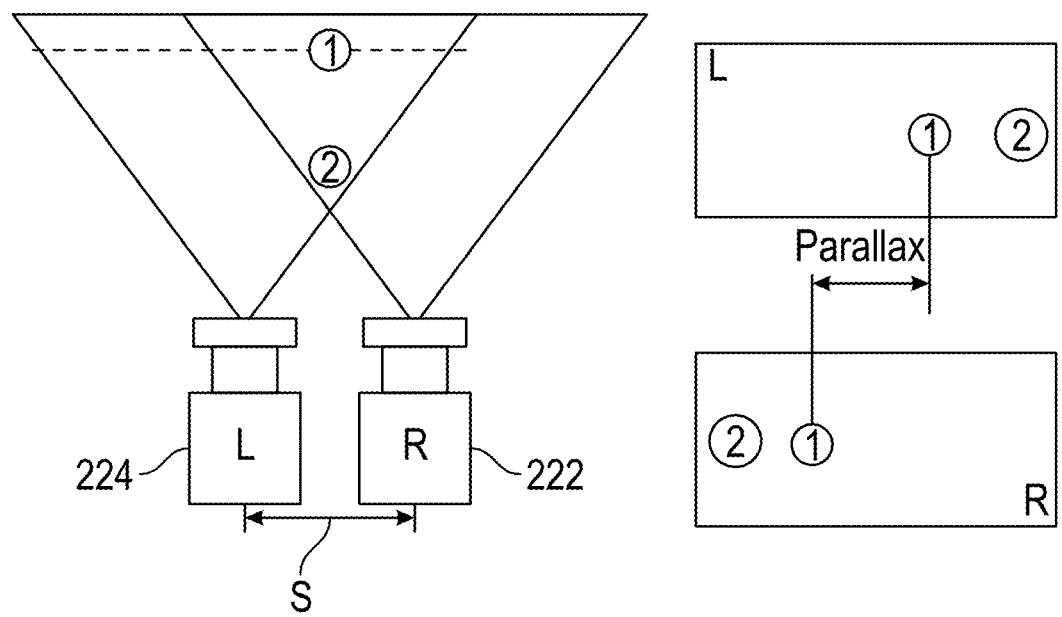
FIG. 4 is a simplified schematic illustrating operation of stereo imaging cameras according to embodiments of the present invention.

Referring now to FIG. 3, the stereo imaging camera 220 includes a first sensor/imager 222, e.g., a right imager, and a second sensor/imager 224, e.g., a left imager. The two sensors 222, 224 located on the same plane and are spaced apart at distance D so that an object distance normal to the plane is the same distance for both sensors 222, 224. The stereo imaging camera 220 takes two images, a left image L and a right image R. Since the distance S between the sensors is known, a comparison of the left image L and the right image R can provide depth information. In particular, the imagers 222, 224 send data to a processor which may be internal or external to the camera 220. The processor in turn calculates depth values for each pixel in the image by the parallax principle, e.g., assessing the disparity between points (e.g., points 1 and 2 depicted in FIG. 4) from the right image R to the left image L.

Figure 5:
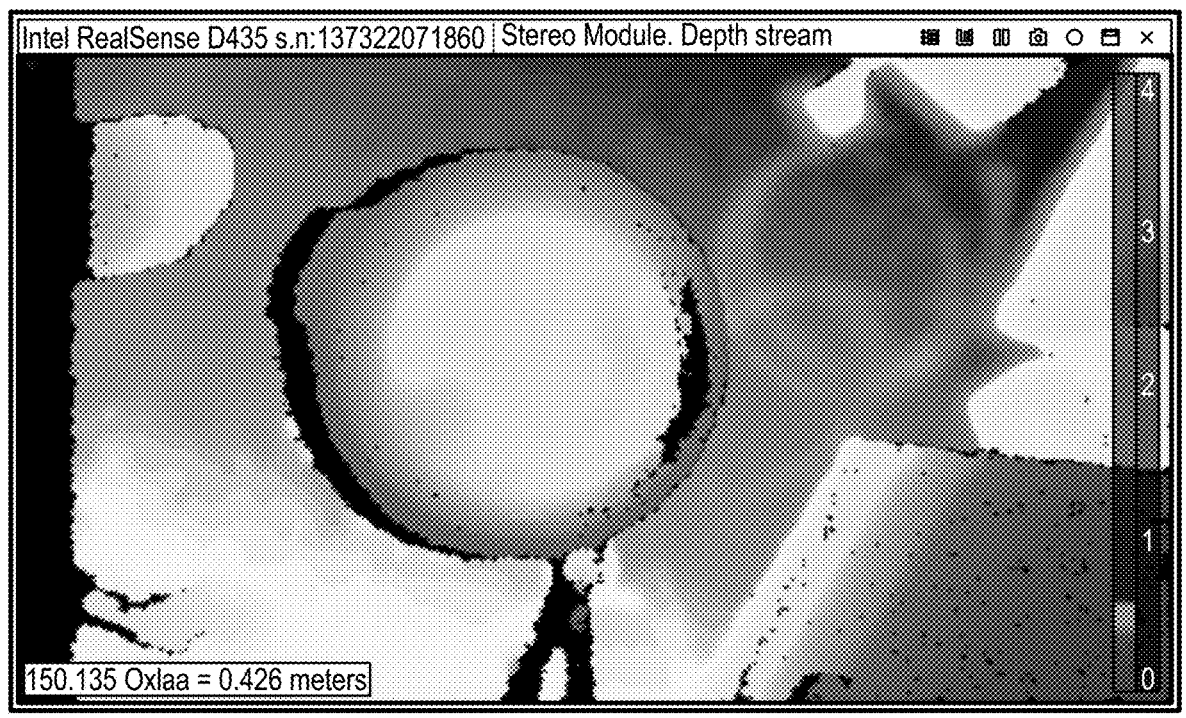
FIG. 5 is an exemplary depth image of foam (reproduced without color) created according to embodiments of the present invention.

The stereo imaging camera 220 then outputs depth images, with each pixel having an associated depth (distance from a parallel plane of the imagers). An example of a depth image is shown at FIG. 5. Although not depicted in color in FIG. 5, depth images are colorized with each color representing a depth from the camera 220. As will be appreciated, various colors may be utilized to represent different depths.

Figure 6:
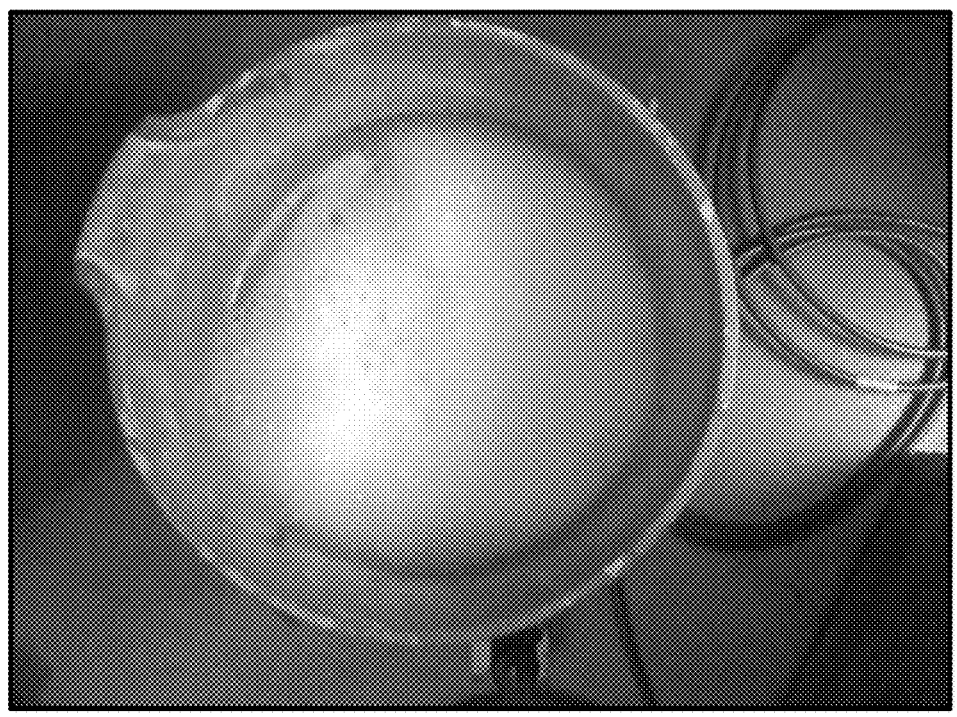
FIG. 6 is an exemplary RGB image (reproduced without color) of foam created in accordance with embodiments of the present invention.
Figure 7:
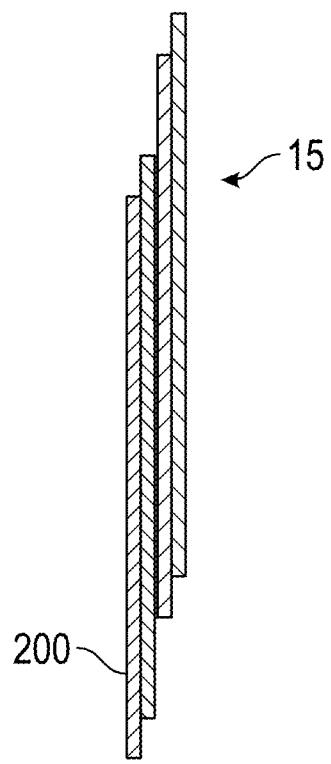
FIG. 7 is a side sectional view of a portion of a wall of a vessel configured for use with embodiments of the present invention.

In embodiments, the camera 220 also includes an RGB module 228 which, as will be appreciated, can capture RGB data and output an RGB image. An exemplary RGB image (decolorized) is shown at FIG. 6. RGB images can be used to supplement the depth data. In particular, RGB images may be used to ascertain the percentage of the surface 142 that contains foam and/or the density of foam present. The images may be manually inspected by an operator to assess/mitigate foam, or RGB images may be output to a controller which automates foam assessment/mitigation via machine learning or the like. In embodiments, the camera 220 may also output a single file with pixels having all four values (RGBD).

The camera 220 may also output stereo image data in a format that also contains color image data (pixel location, RGBD data, and intensity data). This data can be used to assess the percentage of the surface 142 that contains foam and/or the density of foam present.

In certain embodiments, the camera 220 may also include an infrared projector 226. While stereo cameras typically have good low light sensitivity and do not need to supplement ambient lighting, in certain circumstances, e.g., when imaging scenes or objects of low texture or visual detail, e.g., surface that are smooth, infrared light may be used to illuminate an object to collect depth data.

In embodiments, the camera 220 may be USB powered, though other powering mechanisms are possible without departing form the scope of the invention. In certain embodiments, the camera 220 may be secured within a ruggedized housing which may be water resistant and/or cushioned to protect the camera 220.

As will be appreciated, embodiments of the invention are useful in determining when chemical or mechanical defoaming should occur, the amount of defoaming required given the magnitude/rate of formation of foam, and the efficacy of defoaming treatments. In other words, if, for example, the distance of foam to the camera 220 (i.e., the depth) exceeds a certain minimum value or threshold, defoaming may be automatically induced.

Figure 8:
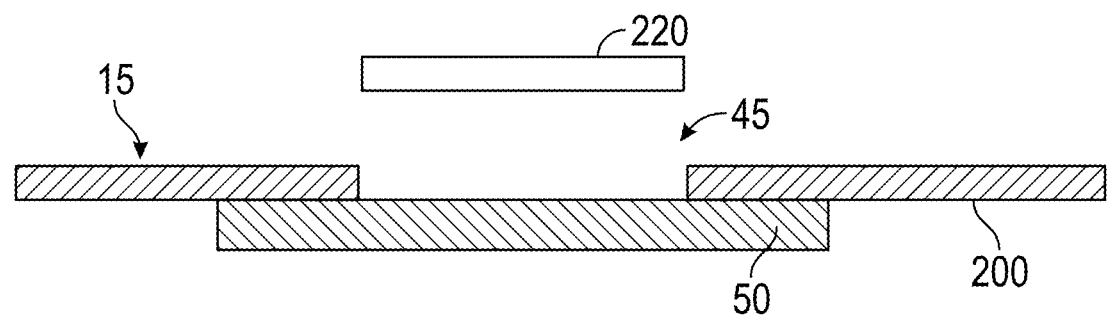
FIG. 8 is a side sectional view of a view port of a vessel configured for use with embodiments of the present invention.

Referring now to FIGS. 2 and 8, in embodiments, the foam identification system 100 includes a vessel 15 having a view port 50 that allows the stereo imaging camera 220 to image the exposed surface 142 of the liquid 144. In some embodiments, the view port 50 may be heated to reduce condensation or may be equipped with an air curtain, as described in greater detail below.

In embodiments, the vessel 15 has a multi-layer film construction that includes an innermost layer of wetted material 200 (e.g., Polyethylene) that is in contact with the liquid in the vessel. The view port 50 may be formed on or bonded to the wetted material 200. In certain embodiments, the view port 50 is made from a low-density polyethylene (LDPE), a material which has been found to have excellent transmissivity in the spectral range of interest, e.g., 380 nm-900 nm. As will be appreciated, the thickness of the view port 50 may vary depending on material properties. Other materials having the requisite transmissivity may be utilized without departing from the scope of the invention. In certain embodiments, polypropylene and polystyrene may be utilized.

In certain embodiments, the view port 50 may be the same single or multi-layer material as the material the vessel 15 itself. In other words, the vessel 15 may not have a dedicated view port having a construction departing from that of the vessel 15. For example, 15 to 20 mil thick LDPE sheeting may provide suitable transmissivity and structure for such embodiments. In yet other embodiments, the port 50 may be the inside wetted material 200 layer and may be formed by simply removing the layers that lie on top of the wetted material 200.

In certain embodiments, the view port 50 is round and is substantially wider/larger in diameter than the lens of the stereo imaging camera 220. Other view port 50 sizes and shapes may be employed without departing from the invention.

As mentioned, the stereo imaging camera 220 may mounted on the support structure 18 such that it is positioned above the vessel 15 and aimed vertically downward such that substantially an entirety of the exposed surface 142 may be imaged. In this regard, the view port 50 may be located on an upper or top surface of the vessel 15. As will be appreciated, the view port 50 may be in a variety of locations, as long as substantially an entirety of the exposed surface 142 may be imaged.

Figure 9:
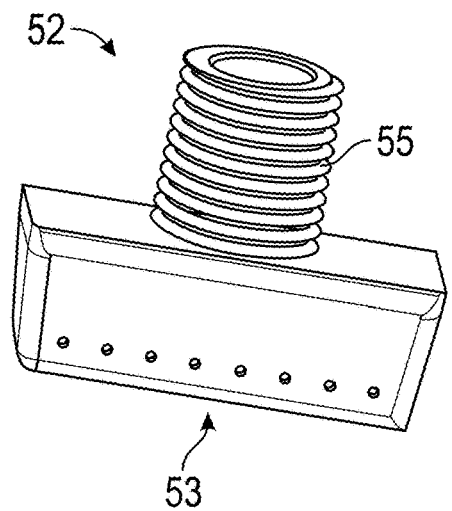
FIG. 9 is an isometric view of an air curtain configured for use with embodiments of the present invention.
Figure 10:
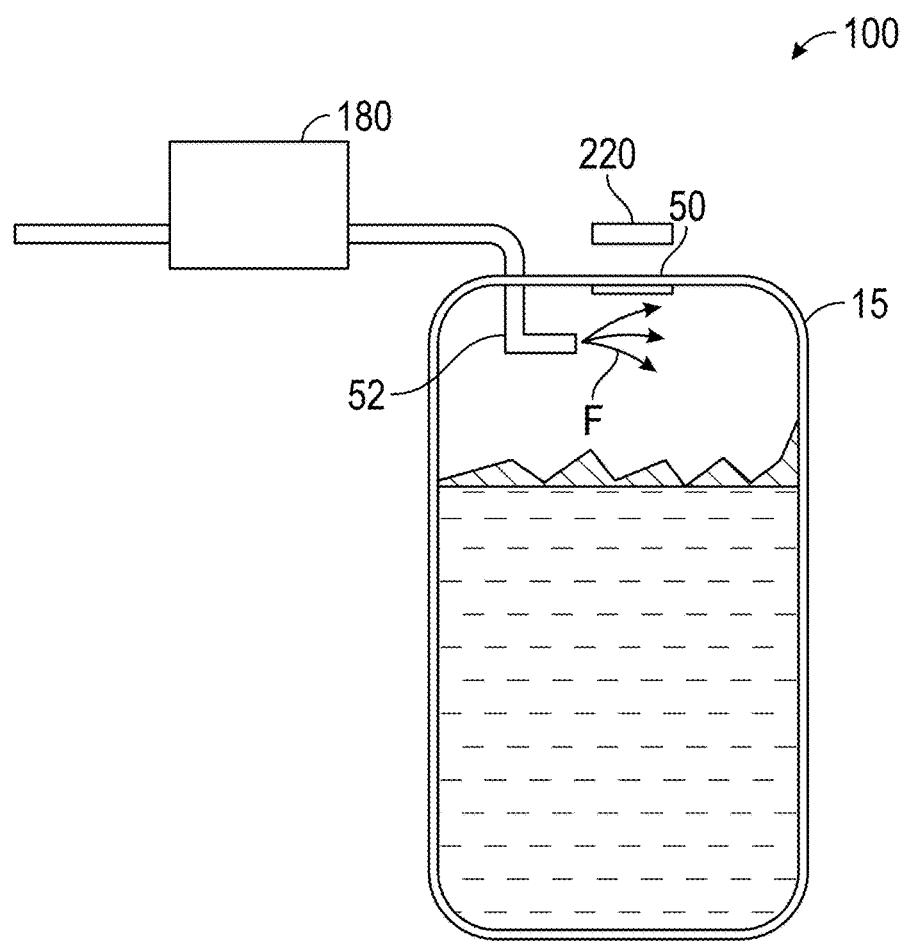
FIG. 10 is a diagram of a foam identification system incorporating an air curtain according to an embodiment of the present invention.

In one embodiment, the foam identification system 100 includes an air curtain 52, as depicted in FIGS. 9 and 10. The air curtain 52 reduces vessel condensation to facilitate stereo imaging of the exposed surface 142. In embodiments, the air curtain 52 is located within the vessel (e.g., bag) 15 and is aimed at the view port 50, or other optically clear view area of the vessel 15. The air curtain 52 may be removable or fixedly attached to a wall of the vessel 15 and may utilize gas (e.g., air, $O_2$ or $N_2$) from existing head-sweep gas flow from the mass flow controller 180. As will be appreciated, in embodiments where the air curtain 52 utilizes existing gas flow, no additional hardware is required, only the addition of the air curtain 52 to the vessel 15. Moreover, existing head-sweep gas flow provides a supply of gas that has a very low dew point of less than −40° C., ideal for condensation prevention.

Referring specifically to FIG. 9 an exemplary air curtain 52 includes a nozzle or outlet portion 53 through which gas/air flow is directed and a threaded base portion 55. The threaded base portion 55 may be directly attached to or otherwise in fluid communication with the mass flow controller 180 (FIG. 10).

In use, the air curtain 52 directs a flow of gas/air F toward the view port 50 to clear the area of condensation. In certain embodiments, the air curtain 52 may be selectively positionable so that the flow of gas F can be directed by an operator to maximize condensation removal. Moreover, the velocity of the flow of gas/air F may be varied depending upon the moisture content of the air in the head space, air temperature in the head space, or other variables. In this regard, the air curtain 52 may be paired with a sensor or meter to measure moisture content and the like.

As will be appreciated, the air curtain 52 may be used to clear a portion of a vessel/bag of condensation for purposes other than imaging, e.g., for various external optical measurements.

In certain other embodiments, an air knife may be employed, though additional pressurized air and flow control may be required in such configurations.

Figure 11:
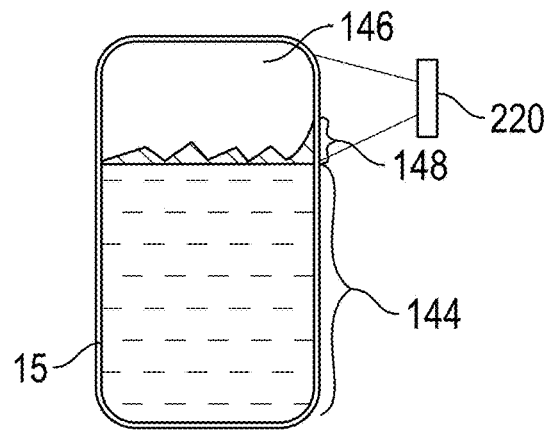
FIG. 11 is a side view of a foam identification system according to an alternative embodiment of the present invention.
Figure 12:
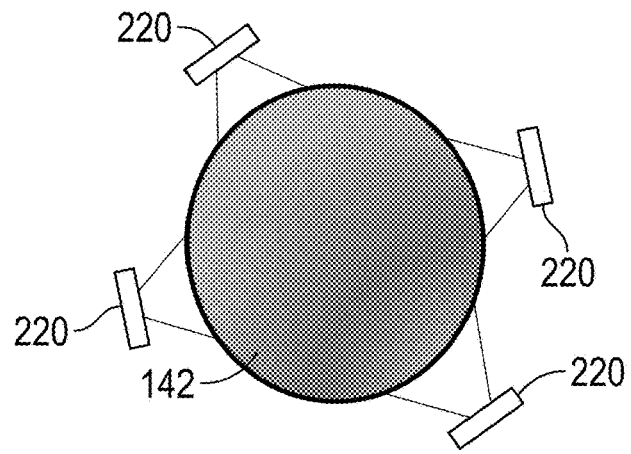
FIG. 12 is a top view of a foam identification system according to an alternative embodiment of the present invention.
Figure 13:
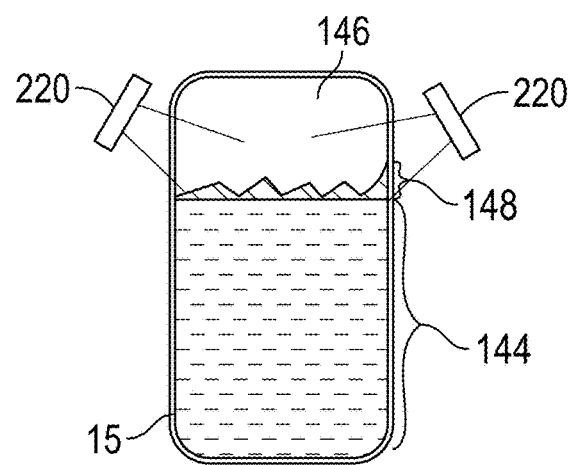
FIG. 13 is a side view of the foam identification system of FIG. 10.

Referring now to FIGS. 11-13, alternative arrangements of stereo cameras may be employed. In one embodiment, the stereo imaging camera 220 may be located such that it images a side of the headspace of the vessel 15. Such an arrangement may be suitable for vessels (e.g., bags) that are entirely made from a material that is substantially transparent in the spectral range of the camera 220, or vessels with a side view port.

In another embodiment, the system may include a plurality of stereo imaging cameras 220 spaced about the periphery of the of the vessel 15 and aimed at the headspace. In certain embodiments, one or more stereo cameras may be built into the rigid bioreactor housing 12. In yet other embodiments, a stereo camera may be integral to the vessel/bag itself. In embodiments, with multiple cameras or cameras built into the vessel/bag, lower resolution stereo imaging cameras may be employed to reduce cost.

In use, the system 100 identifies the presence of and/or a magnitude of foam 148 on the surface 142 of the liquid 144 exposed to the headspace 146 in several ways. In one embodiment, the system 100 detects a difference between a depth of the surface 142 without foam, and a depth measurement during use of the vessel/reactor that is indicative of a level of foam that is potentially problematic. In other embodiments, the rate of depth change may be assessed via multiple measurements by the stereo imaging camera 220.

A method of identifying foam 148 on a surface of a liquid 144 in a vessel 15 is provided. The method includes taking a depth measurement D of the surface 142 of liquid 144 via the stereo imaging camera 220 without the presence of foam 148 in the vessel 15 and then obtaining at least one depth measurement D' of a surface 142 to detect a change in depth of the exposed surface 142 of the liquid 144 and identifying foam 148 on the exposed surface 142 based on the detected depth change.

In yet another embodiment, the step of identifying foam 148 on the exposed surface 142 includes obtaining a plurality of depth measurements of, for example, a set area on the exposed surface 142 of the liquid 144, determining a rate of depth change of the area on the exposed surface 142 from the plurality of depth measurements of the exposed surface 142, and identifying the presence and/or a magnitude of foam 148 on the surface of the liquid 144 by comparing the rate of depth change to a predetermined value that is indicative of foam.

In one embodiment, the method of identifying foam 148 also includes mitigating detected foam 148 on the exposed surface 142 of the liquid 144, for example, by application of an antifoaming agent into the vessel 15.

In embodiments, the method of identifying foam 148 also includes removing condensation from the view port 50 of vessel 15 via a condensation prevention system (e.g., the air curtain 52, etc.) to facilitate identification of foam 148 by the stereo imaging camera 220.

In some embodiments, the foam identification system 100 provides de-foaming injection feedback, by analyzing the foam magnitude during and after use of mechanical or gaseous solutions in addition to chemical anti-foam agents. The stereo imaging camera 220 provides data that quantifies an input of anti-foam agents and/or a response of the foam 148 to the anti-foam agents.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A bioreactor system comprising:
   a housing configured to house and support a vessel;
   a stereo camera having first and second imagers secured to the housing, the stereo camera configured to image a surface of a liquid and a foam exposed to a headspace of the vessel;
   a controller operatively connected to the stereo camera; and
   wherein the stereo camera and controller are configured to create an image of the exposed surface and identify foam on the surface based on the image.

2. The bioreactor system of claim 1, wherein the image of the exposed surface is a depth image.

3. The bioreactor system of claim 1, wherein the stereo camera further comprises an RGB module and the image is an RGB image.

4. The bioreactor system of claim 3, wherein the image is a composite depth and RGB image.

5. The bioreactor system of claim 1, wherein the stereo camera further comprises an infrared projector to facilitate depth imaging of surfaces that have low texture or visual detail.

6. The bioreactor system of claim 5, wherein the stereo camera detects light having a wavelength of from about 400 nm to about 865 nm.

7. The bioreactor system of claim 1, wherein the stereo camera has a field of view from about 70° to about 120°.

8. The bioreactor system of claim 1, wherein the stereo camera provides data that quantifies an input of anti-foam agents and/or a response of the foam to the anti-foam agents.

9. The bioreactor system of claim 1, further comprising:
   a vessel having a view port configured to allow the stereo camera to image the exposed surface.

10. The bioreactor system of claim 9, wherein the view port is heated to reduce condensation.

11. The bioreactor system of claim 1, further comprising:
    an air curtain configured to reduce vessel condensation to facilitate imaging of the exposed surface.

12. The bioreactor system of claim 11, further comprising the vessel; and
    wherein the air curtain is located within the vessel.

13. The bioreactor system of claim 1, wherein the camera is mounted on a support structure of the housing so that it is positioned above the vessel and aimed vertically downward so that substantially an entirety of the exposed surface may be imaged.

14. The bioreactor system of claim 1, wherein the vessel is a collapsible bioreactor bag.

15. A method of identifying foam on a surface of a liquid in a vessel comprising the steps of:
   generating an image of a surface of the liquid that is exposed to the headspace of the vessel via a stereo imaging camera having first and second imagers;
   identifying foam on the exposed surface based on the image.

16. The method of claim 15, wherein the image of the exposed surface is a depth image.

17. The method of claim 16, wherein the step of identifying foam on the exposed surface comprises:
   comparing a first depth image of the surface of the liquid without foam to a second depth image of the surface to determine whether the depth has changed.

18. The method of claim 16, wherein the step of identifying foam on the exposed surface comprises:
   obtaining a plurality of depth images of the exposed surface of the liquid,
   determining a rate of depth change on the exposed surface from the plurality of depth images of the exposed surface, and
   identifying the presence and/or a magnitude of foam on the surface by comparing the rate of depth change to a predetermined value that is indicative of foam.

19. The method of claim 15, wherein the stereo camera further comprises an RGB module and the image is an RGB image.

20. The method of claim 19, wherein the image is a composite depth and RGB image.

21. The method of claim 15, wherein the stereo camera further comprises an infrared projector to facilitate depth imaging of surfaces that have low texture or visual detail.

22. The method of claim 15, further comprising providing data that quantifies an input of anti-foam agents and/or a response of the foam to the anti-foam agents.

23. The method of claim 15, further comprising the step of:
   mitigating detected foam on the exposed surface of the liquid.

24. The method of claim 15, further comprising the step of:
   removing condensation from the vessel via a condensation prevention system to facilitate identification of foam by the stereo camera.

* * * * *